United States Patent
Song et al.

(10) Patent No.: US 6,786,097 B2
(45) Date of Patent: Sep. 7, 2004

(54) ULTRASOUND IMAGING SYSTEM AND METHOD USING WEIGHTED CHIRP SIGNALS

(75) Inventors: Tai Kyong Song, Seoul (KR); Dong Yeul Kim, Seoul (KR)

(73) Assignee: Medison Co. LTD, Kangwon-Do (KR)

( * ) Notice: Subject to any disclaimer, the term of this patent is extended or adjusted under 35 U.S.C. 154(b) by 0 days.

(21) Appl. No.: 10/184,727

(22) Filed: Jun. 27, 2002

(65) Prior Publication Data

US 2003/0115963 A1 Jun. 26, 2003

(30) Foreign Application Priority Data

Dec. 26, 2001 (KR) ........................................ 2001-84959

(51) Int. Cl.$^7$ ............................................. G01N 29/06
(52) U.S. Cl. ............................. 73/602; 73/625; 73/626; 600/443; 600/447
(58) Field of Search ........................... 73/606, 602, 626, 73/625; 600/443, 447

(56) References Cited

U.S. PATENT DOCUMENTS

| | | | | |
|---|---|---|---|---|
| 4,949,312 A | * | 8/1990 | Iwasawa | 367/7 |
| 4,949,313 A | * | 8/1990 | Iwasawa | 367/7 |
| 5,793,703 A | * | 8/1998 | Shippey | 367/88 |
| 2002/0005071 A1 | * | 1/2002 | Song et al. | 73/606 |

FOREIGN PATENT DOCUMENTS

| | | | | |
|---|---|---|---|---|
| JP | 02271845 A | * | 11/1990 | ............ A61B/8/14 |
| JP | 8024258 | | 1/1996 | |
| JP | 9187457 | | 7/1997 | |
| JP | 09187457 A | * | 7/1997 | ............ A61B/8/00 |
| JP | 2001-9833 | | 1/2001 | |
| WO | 00/57791 | | 10/2000 | |

OTHER PUBLICATIONS

Information Notice from Japanese Patent Office, application No. 2001–402092, date of mailing Dec. 12, 2003, No translation provided.

* cited by examiner

Primary Examiner—Hezron Williams
Assistant Examiner—Rose M. Miller
(74) Attorney, Agent, or Firm—Thelen Reid & Priest LLP; David B. Ritchie

(57) ABSTRACT

An ultrasound imaging system and method for making a harmonic image of a good SNR (signal-to-noise ratio) by effectively removing fundamental frequency components through a pulse-compressing using weighted chirp signals, is provided. The ultrasound imaging system includes: a transducer array for converting weighted chirp signals to ultrasound signals, and transmitting the ultrasound signals to a target object; a receiver for receiving signals reflected from the target object; a pulse-compressor for selectively pulse-compressing fundamental frequency components or harmonic frequency components in the reflected signals; and a producer for producing receive-focused signals from the pulse-compressed signals. Therefore, the ultrasound imaging system can form ultrasound image using the fundamental frequency components, and can form ultrasound harmonic image using the harmonic frequency components according to 2fo-correlation method or 2fo-correlation (PI) method.

18 Claims, 6 Drawing Sheets

ULTRASOUND IMAGING SYSTEM AND METHOD USING WEIGHTED CHIRP SIGNALS

FIELD OF THE INVENTION

The present invention relates to an ultrasound imaging system and method thereof, more particularly, to a pulse-compression based on ultrasound imaging system and method that generates a harmonic image with an enhanced signal-to-noise ratio (SNR) by effectively removing fundamental frequency components through pulse-compression using weighted chirp signals.

BACKGROUND OF THE INVENTION

The ultrasound imaging system is widely used in the medical field for displaying an image of a target object, such as a human body. Ultrasound signals are transmitted to the target object and then reflected from the target object, thereby forming the ultrasound image.

For transmission of the ultrasound signals, the ultrasound imaging system generally includes a transducer array, which includes a plurality of transducers and a pulser for driving each transducer. Each transducer generates ultrasound signals in response to the pulse applied from the pulser. During transmission of the ultrasound signal, the timing of generating the ultrasound signal at each transducer is controlled, thereby transmit-focusing the ultrasound signals at a predetermined position within the target object. In other words, the pulser pulses the respective transducers with different time delays so that the ultrasound signals reach a desired position within the target object at the same time.

The ultrasound signals reflected from the target object are received by the transducer array. The time for the reflected signals to reach the respective transducers is different depending on the distance between the transducers and the target object. Therefore, in order to compensate for the time difference among the transducers, a beamformer applies time delays, with respect to the reflected signals, which are received by the respective transducers, and generates receive-focused signals.

The power of the received signals is remarkably lowered when the ultrasound signal passes through a highly dense medium, such as a human body. As a result, when the target object is located deep in the body, the desired information is difficult to obtain with the above-mentioned ultrasound imaging apparatus. Most of the ultrasound imaging apparatuses currently being used generate ultrasound signals by applying a pulse of short duration to the transducers. Increasing the peak voltage of the pulse may solve problems due to the attenuation of the ultrasound signals. However, there is a certain limit to increasing the peak voltage of the pulse since this may affect the internal organs of the human body.

Ultrasound signals are distorted by various nonlinear characteristics of the propagation medium, which give rise to phenomena such as diffraction and attenuation. These nonlinear characteristics distort a transmitted ultrasound signal to generate harmonic frequency components of the signal frequency. The imaging technique using harmonic frequency components is called "ultrasound harmonic imaging technique". In general, harmonic frequency components are generated at integer multiples of the fundamental frequency components. The nonlinear propagation of ultrasound waves can be modeled via the Khokhov-Zabolotskaya-Kuznetsov (KZK) equation, which can be solved by a finite difference approximate scheme.

The ultrasound harmonic imaging technique is geared to forming an ultrasound image by using a second harmonic frequency component that is produced by the nonlinear characteristics of the medium in response to transmission of a short pulse. Thus, forming an ultrasound image by using harmonic frequency components has proven to produce an ultrasound image having an improved resolution, SNR and contrast as compared to an ultrasound imaging method using only a fundamental frequency component. Therefore, the ultrasound imaging method using harmonic frequency components forms an ultrasound image of better image quality than the method using a fundamental frequency component.

Since the harmonic frequency components are generated in proportion to the intensity of the sound pressure, and the magnitude of the harmonic frequency components are much lower than the fundamental frequency component, an ultrasound signal with sufficient sound pressure should necessarily be used as a transmission signal. However, conventional ultrasound harmonic imaging techniques employ a short pulse signal so there is a limit to increasing the sound pressure of the ultrasound transmission signal and the SNR. If the sound pressure of the ultrasound signals increases to above predetermined threshold value, then a saturation phenomenon arises wherein harmonic frequency components are not increased any more. Accordingly, conventional ultrasound imaging methods cannot improve the SNR of a harmonic image, typically, a second harmonic image beyond a predetermined level by increasing the sound pressure of the ultrasound transmission signal.

In order to form an ultrasound image of high quality with an ultrasound harmonic imaging technique, the fundamental frequency component should be removed and harmonic frequency components extracted from the received ultrasound signal. For such purposes, general filtering method, such as those using a band-pass-filter (BPF) or high-pass-filter (HPF) is commonly used.

However, if the frequency band of the fundamental frequency components overlap with the harmonic frequency components, then the harmonic frequency components may undesirably be filtered out in proportion to the overlapping bandwidth, or the fundamental frequency components not completely removed, thereby deteriorating the SNR and resolution of the ultrasound image. To circumvent the drawbacks associated with the filtering method, the pulse inversion method may alternatively be used which revealed to be more effective in eliminating a fundamental frequency component than the filtering method.

The pulse inversion method transmits two ultrasound signals, a positive polarity pulse and a negative polarity pulse, that have a phase difference of 180° from each other along every scan line, and then adds the two received ultrasound signals, thereby effectively removing the fundamental frequency component.

However, the pulse inversion method also has problems from the system perspective since two transmit-receive steps are required to form one scan line, and therefore, the frame rate is cut in half when the pulse inversion method is applied for all the scan lines.

To avoid the limitation on transmission sound pressure and increase the ultrasound penetration distance, a conventional fundamental frequency imaging method may employ pulse compression. An ultrasound imaging system employing a pulse compression method uses a coded long pulse of a long duration time instead of a conventional short pulse. In such an ultrasound imaging system influences the system a particular pulse being used influences the system performance to a great degree. That is, the ultrasound image quality is affected by how well matched the frequency band of the used signal is to the limited band characteristic of the transducer array.

System performance is further affected by the specific configuration of the correlator or pulse-compressor in an ultrasound receiver. Note that where coded long pulses are used, the correlator or pulse-compressor is used to give the same effects as the short pulse.

The conventional ultrasound imaging system employing pulse compression includes a single correlator matched to the fundamental frequency component in the ultrasound receiver so that an ultrasound image is formed with only the fundamental frequency component. Accordingly, a harmonic image cannot be formed with the conventional ultrasound imaging system. Thus, the quality of a conventional ultrasound image is lowered.

The reason why only a single correlator only matched to the fundamental frequency component has been inevitably used is that the magnitudes of the harmonic frequency components in the received ultrasound signal are very low relative to that of the fundamental frequency component so that it is not feasible to extract the harmonic frequency components from the received ultrasound signal. The additional reason that oars using multiple correlators in the ultrasound receiver lies in that an appropriate signal is not yet available which matches well to the limited band characteristics of the transducer array. Even though spread spectrum signal, such as a chirp signal, may reasonably be matched to the limited band characteristics of the transducer array, such a general chirp signal, if subjected to a correlator results in a peak sidelobe whose gain is that of lower than a mainlobe by approximately −13 dB. However, for medical ultrasound imaging applications, the output signal of a pulse-compressor should have sidelobes of −50 dB or less. So, the general chirp signal is not well matched to the specifications of medical ultrasound imaging systems.

SUMMARY OF THE INVENTION

It is, therefore, an objective of the present invention is to provide an ultrasound imaging system and method to generate a harmonic image with an enhanced SNR(signal-to-noise ratio) by effectively removing a fundamental frequency component through pulse-compression using weighted chirp signals.

Another objective of the present invention is to provide an ultrasound imaging system and method that increase the SNR of a harmonic image by extending the length of a weighted chirp signal using a weighted chirp signal, which is to be transmitted in a form of ultrasound signals.

Still another objective of the present invention is to provide an ultrasound imaging system and method that selectively pulse-compresses only harmonic frequency components by transmitting ultrasound signals converted from weighted chirp signals and allowing RF samples received at each transducer to pass through a correlator matched with harmonic frequency components of the transmitted ultrasound signals.

According to one aspect of the present invention, an ultrasound imaging system includes: a transducer array for converting weighted chirp signals to ultrasound signals, and transmitting the ultrasound signals to a target object; a receiver for receiving signals reflected from the target object; a pulse-compressor for pulse-compressing harmonic frequency components of the ultrasound signals in the reflected signals; and means for producing receive-focusing the pulse-compressed signals.

The pulse-compressor further includes: a selector for selecting the harmonic frequency components in the reflected signals; and a correlator for pulse-compressing the selected harmonic frequency components.

According to another aspect of the present invention, an ultrasound imaging method includes the steps of: converting weighted chirp signals to ultrasound signals; transmitting the ultrasound signals to a target object; receiving signals reflected from the target object; pulse-compressing harmonic frequency components of the ultrasound signals in the reflected signals; and receive-focusing the pulse-compressed signals.

The pulse-compressing step further includes selecting the harmonic frequency components in the reflected signals; and pulse-compressing the selected harmonic frequency components selected by the selector.

According to still another aspect of the present invention, an ultrasound imaging system includes: a transducer array for converting weighted chirp signals to ultrasound signals, and transmitting the ultrasound signals to a target object; a receiver for receiving signals reflected from the target object; a pulse-compressor for selectively pulse-compressing fundamental frequency components or harmonic frequency components of the ultrasound signals in the reflected signals; and means for receive-focusing the pulse-compressed signals.

The pulse-compressor further includes: a first correlator for pulse-compressing the fundamental frequency components; a second correlator for pulse-compressing the harmonic frequency components; and a mode selector for selecting the fundamental frequency components or the harmonic frequency components in the reflected signals and for enabling the selected frequency components to be pulse-compressed via one of the first and second correlators.

According to still another aspect of the present invention, an ultrasound imaging method includes the steps of: converting weighted chirp signals to ultrasound signals, and transmitting the ultrasound signals to a target object; receiving signals reflected from the target object; pulse-compressing fundamental frequency components or harmonic frequency components of the ultrasound signals in the reflected signals; and receive-focusing the pulse-compressed signals.

The pulse-compressing step further includes the steps of: selecting the fundamental frequency components or the harmonic frequency components in the reflected signals; and pulse-compressing the selected frequency components.

BRIEF DESCRIPTION OF DRAWINGS

The above and other objects and features of the present invention will become apparent from the following description of the preferred embodiments given in conjunction with the accompanying drawings.

DETAILED DESCRIPTION OF THE PRESENT INVENTION

Preferred embodiments of the present invention will now be described with reference to the accompanying drawings.

Ultrasound signals are distorted by the nonlinear characteristics of the medium through which it is passing. The nonlinear propagation of ultrasound waves can be modeled via the Khokhov-Zabolotskaya-Kuznetsov (KZK) equation, which can be solved by a finite difference approximate scheme. The KZK equation explains various nonlinear characteristics such as diffraction of sound pressure, attenuation of sound pressure, and generation of a harmonic frequency component, and models the shape of an ultrasound signal as a sound pressure given such parameters as initial transmission sound pressure, propagated distance, and medium. The KZK equation is a numerical modeling means for predicting or explaining ultrasound propagation in an actual medium.

Assuming that a circular disc transducer is used and the ultrasound signals are symmetrically transmitted from the center of the transducer, the sound pressure $$\left(\frac{\partial^2 p}{\partial z \partial t'}\right)$$

of an ultrasound signal is represented by the KZK equation:

$$\frac{\partial^2 p}{\partial z \partial t'} = \frac{c_o}{2}\left(\frac{\partial^2 p}{\partial z r^2} + \frac{1}{r}\frac{\partial p}{\partial r}\right) + \frac{\partial}{2c_0^3}\frac{\partial^3 p}{\partial t'^3} + \frac{\beta}{2\rho_o c_0^3}\frac{\partial^2 p^2}{\partial t'^2} \quad \text{Eq. 1}$$

...□... ...□... ...□...

where p is a sound pressure, z is a proceeding direction of ultrasound signals, r is a radial axis orthogonal to the z-axis, t' is a delay time and corresponds to $t-z/c_o$, $c_o$ is the ultrasound speed in the medium, ∂ is a spreading degree, β is a nonlinear constant, and $\rho_o$ is a density of the medium.

In Eq. 1, the first term □represents the diffraction of the sound pressure of the ultrasound signal, the second term □represents the attenuation of the ultrasound signals, and the third term □represents the density of the medium. In generating a second harmonic frequency component, the third term □may be approximated as a second-order polynomial:

$$r(t) \cong a_1 s(t) + a_2 s(t)^1 \quad \text{Eq. 2}$$

where r(t) is the received ultrasound signal, s(t) is the transmitted ultrasound signal, and $a_1$ and $a_2$ are predetermined constants.

Figure 1:
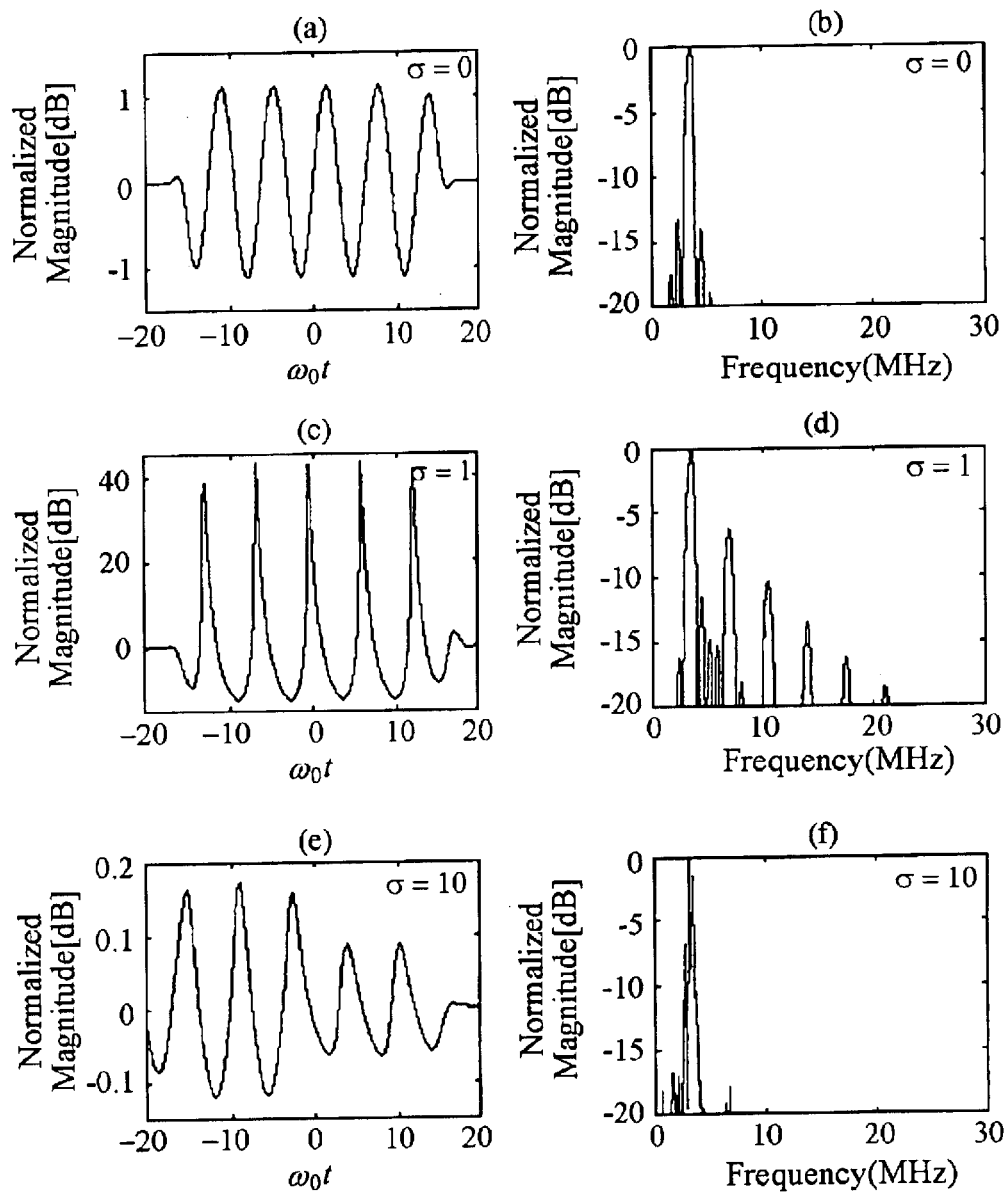
FIG. 1 illustrates axial direction waveforms calculated by using the Khokhlov-Zabolotskaya-Kuznetsov (KZK) equation.

FIG. 1 illustrates axial direction waveforms calculated by using the KZK equation. FIGS. 1(a), (c) and (e) illustrate axial direction waveforms of signals measured at various depths. FIGS. 1(b), (d) and (f) illustrate the frequency spectrums of the axial direction waveforms of FIGS. 1(a), (c) and (e), respectively. The x-axis represents the frequency of the ultrasound signal. The y-axis represents the sound pressure of the ultrasound signal.

The axial direction waveforms (a), (c), and (e) and the frequency spectrums (b), (d), and (f) are produced using a circular disc transducer having a fixed focal length of 63.5 mm, radius of 25.4 mm, and center frequency of 3.5 MHz, when a burst sinusoidal function with a center frequency of 3.5 MHz is transmitted at an initial transmission sound pressure Po of 175 kPa during a duration time of 5/fo. In FIG. 1, σ is the ratio of a proceeding distance z to a focal length d, and is expressed as σ=z/d. For example, if σ=0 then z=0 (at the source). If σ=1 then z=d (proceeding distance is one focal length).

FIG. 1(a) illustrates the waveform of the ultrasound transmission signal at the source (σ=0). FIG. 1(c) illustrates the waveform of the ultrasound signal measured at one focal length distance (σ=1). A signal transmitted to one focal length contains many harmonic frequency components because of the nonlinear characteristics of the medium so that the signal is distorted as shown in FIG. 1(c). FIG. 1(e) illustrates the waveform of the signal measured at σ=10. The sound pressure is attenuated. This attenuation is higher in a high frequency component, and lower in a low frequency component. As shown in FIG. 1(f), this signal has few harmonic frequency components.

To produce ultrasound harmonic images of high quality, the sound pressure should be increased to amplify the harmonic frequency components. However, because of saturation, the sound pressure cannot be raised past the saturation limit. Thus, a new method is desirable for improving the SNR of a harmonic image without having to raise the sound pressure.

Figure 2:
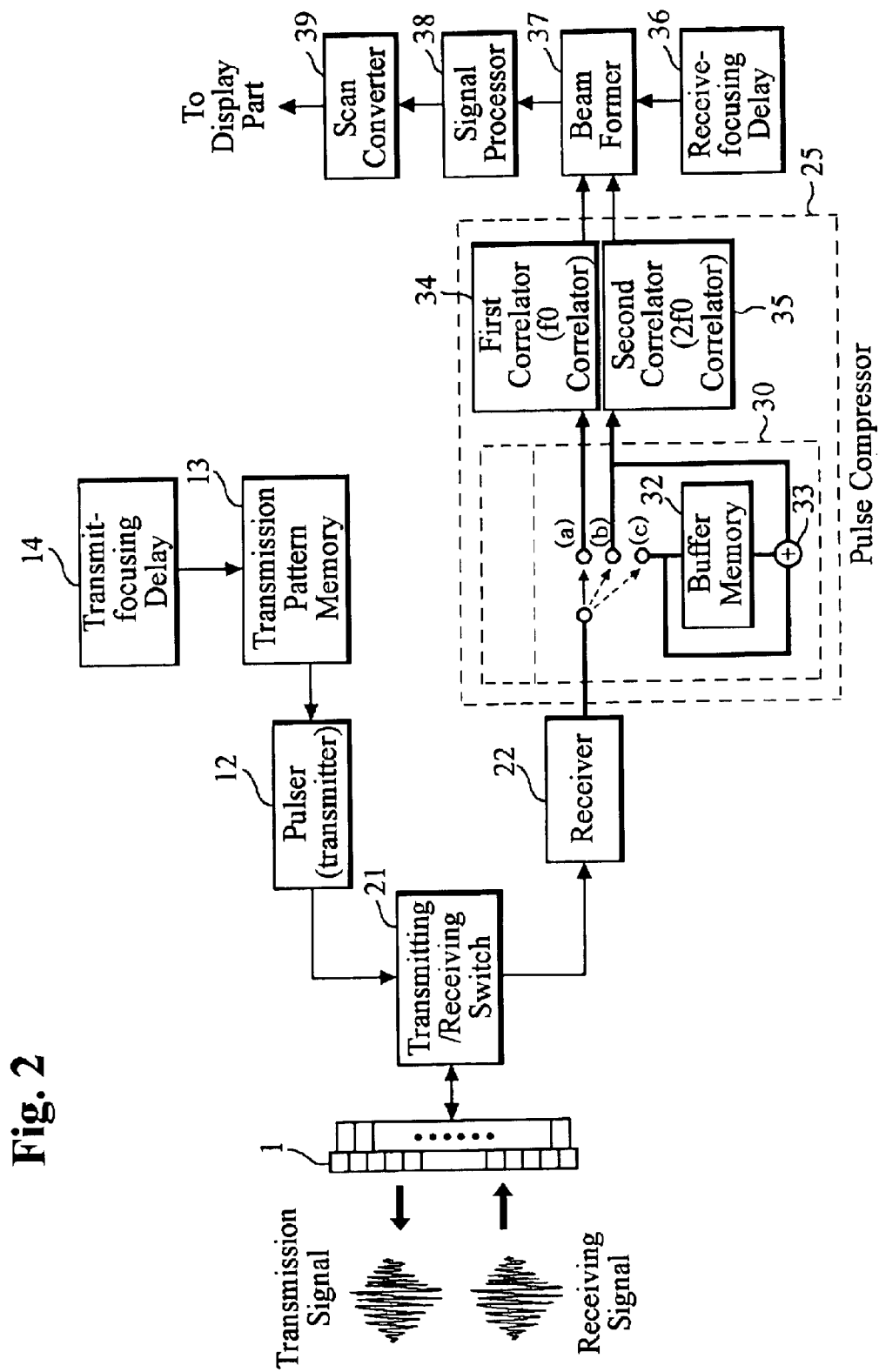
FIG. 2 illustrates a block diagram of an ultrasound imaging system using weighted chirp signals in accordance with the present invention.

Referring to FIG. 2, when transmitting/receiving ultrasound signals in accordance with the present invention, a chirp signal weighted by a Hanning window function is used as the pulse compressed signal, rather than a general linear chirp signal. A weighted chirp signal s(t) is a linear chirp signal multiplied by a window function:

$$s(t) = \omega_1(t) e^{i(\omega_o t + \frac{\mu}{2}t^2)} \quad \text{Eq. 3}$$

where $\omega_1(t)$ is the window function, $\omega_o$ is the center frequency of the chirp signal, and $\mu(=\Delta\omega/\Delta T)$ is the time rate of change of the frequency.

Pulser or ultrasound transmitter 12, takes a transmission signal pattern stored in transmission orthogonal code pattern memory 14, amplifies the pattern and transfers it to transducer array 1. Pulser 12 linearly amplifies arbitrary signals. Transmission pattern memory 13 stores the weighted chirp signal as a transmission signal pattern. Transmission pattern memory 13 is connected to means for selecting a window function used to adjust the mainlobe and sidelobe width of the pulse-compressed signal. Therefore, the chirp signals can be selectively weighted by any one of various window functions, such as Hanning, Hamming, and Blackman window functions.

The weighted chirp signals transmitted by transducer array 1 are distorted while passing through the medium. The distorted signals are received at transducer array 1 and then transmitted to receiver 22. Transmitting/receiving switch 21 acts as a duplexer that protects receiver 22 from high voltage power released from pulser 12. When transducer array 1 performs transmission and reception, switch 21 properly switches transducer array 1 between pulser 12 and receiver 22.

If the weighted chirp signals pass through a system having nonlinear characteristics, then the received signal r(t) is:

$$r(t) = a_1 w_1(t) e^{j(\omega_0 t + \frac{\mu}{2} t^2)} + a_2 w_1^2(t) e^{j(2\omega_0 t + \mu t^2)} \quad \text{Eq. 4}$$

where $\omega_1(t)$ is a window function, $\omega_o$ is the center angular frequency of the chirp signal, $\mu(=\Delta\omega/\Delta T)$ is the time rate of change of the frequency, and $a_1$, and $a_2$ are predetermined constant.

The received signal r(t) includes second harmonic frequency component 2fo as well as fundamental frequency component fo. The signals received at each transducer of transducer array 1 are transmitted to pulse compressor 25 via receiver 22. Pulse-compression about each frequency component is separately performed by first correlator 34 matched with fundamental frequency component fo or second correlator 35 matched with second harmonic frequency component 2fo.

Beamformer 37 receives pulse-compressed signals from pulse compressor 25 and receive-focuses them with reference to the delay values of receive-focusing delay 36. Signal processor 38 produces signals capable of forming B-mode images by performing envelope detection and log compression. Scan converter 39 converts the B-mode image into an image format to display on an actual monitor.

Pulse compressor 25 includes mode selector 30 for switching operational modes to selectively pulse-compress the frequency components of the received signal through one of three paths; first correlator 34 (i.e., fo correlator) for pulse-compressing the fundamental frequency component of the received signal; second correlator 35 (i.e., 2fo correlator) for pulse-compressing the second harmonic frequency component of the received signal; and buffer memory 32. The three operational modes are selected by first input terminal (a), second input terminal (b), and third input terminal (c) of mode selector 30.

First input terminal (a) is used for the fundamental frequency correlation (i.e., fo-correlation) mode to pulse-compress the fundamental frequency component. Second input terminal (b) is used for the harmonic frequency correlation (i.e., 2fo-correlation) mode to pulse-compress the harmonic frequency component so that an ultrasound harmonic image is obtained without reduction in frame rate. Second input terminal (b) is very useful where the bandwidth of the weighted chirp signal is narrower than a predetermined width.

Third input terminal (c) is used for the harmonic frequency correlation pulse inversion (i.e., 2fo-correlation(PI)) mode to pulse-compress the harmonic frequency component by a pulse inversion method. Third input terminal (c) is used to obtain ultrasound harmonic images where the concern is with improvement of resolution rather than frame rate and is very useful with weighted chirp signals of wide bandwidth.

First correlator 34 is matched to the fundamental frequency component fo of the received signal and connected to first input terminal (a) to perform the fundamental frequency correlation (i.e., fo-correlation).

Second correlator 35 is matched to the harmonic frequency component 2fo of the received signal and connected to second input terminal (b) or third input terminal (c) to selectively perform the harmonic frequency correlation (i.e., 2fo-correlation) or the harmonic frequency correlation pulse inversion (i.e., 2fo-correlation (PI)).

The impulse response function h(t) of second correlator 35 is represented by:

$$h(t) = \omega_1^2(t) e^{j(2\omega_0 t + \mu t^2)} \quad \text{Eq. 5}$$

where $\omega_1(t)$ is a window function, $\omega_o$ is the center angular frequency of the chirp signal, and $\mu(=\Delta\omega/\Delta T)$ is the time rate of change of the frequency.

The impulse response function h(t) is a squared format of the transmission weighted chirp signal s(t) and is used as a reference signal when the received signal is pulse-compressed by second correlator 35 matched with second harmonic frequency component 2fo.

In the fundamental frequency correlation (fo-correlation) mode, through first input terminal (a), the received signal is transmitted to first correlator 34 matched with fundamental frequency component fo of the transmitted weighted chirp signal. Therefore, first correlator 34 removes harmonic frequency component 2fo and pulse-compresses fundamental frequency component fo.

In the harmonic frequency correlation (2fo-correlation) mode, through the second input terminal (b), the received signal is transmitted to second correlator 35 matched with harmonic frequency component 2fo of the transmitted weighted chirp signal. Therefore, second correlator 35 removes fundamental frequency component fo and generates a harmonic image.

In the harmonic frequency correlation pulse inversion (2fo-correlation(PI)) mode, through the third input terminal (c), the weighted chirp signal s(t) of Eq. 3 is transmitted and the received signal stored in buffer memory 32. A phase inversion signal −s(t) of the weighted chirp signal s(t) is transmitted and received at receiver 22. Adder 33 adds the received signal from receiver 22 and the pre-stored weighted chirp signal from buffer memory 32 and removes fundamental frequency component fo. The signal obtained by the pulse inversion (PI) method is transmitted to second correlator 35 and pulse-compressed to make a harmonic image.

The pulse compressed signal through second correlator 35 is $$y(t) = a_2 e^{j(2\omega_0 t + \mu t^2)} \int_{-\infty}^{\infty} \omega_1^2(t+\tau) \omega_1^{*2}(\tau) e^{j2\mu\tau\tau} d\tau + C_{02}(t) \quad \text{Eq. 6}$$

with the same parameters as mentioned in Eqs. 1–6 such that $$c_{02}(t) = a_1 e^{j(\omega_0 t + \frac{\mu}{2} t^2)} \int_{-\infty}^{\infty} \omega_1(t+\tau) \omega_1^{*2}(\tau) e^{-j\tau(\omega_0 - \mu t + \frac{\mu}{2}\tau)} d\tau \quad \text{Eq. 7}$$

where $C_{o2}(t)$ is a cross-correlation function between fundamental frequency component fo of the received signal and the impulse response function h(t) of second correlator 35. If the frequency band of fundamental frequency component fo does not overlap with that of second harmonic frequency component 2fo of the transmission signal, then the value of $C_{o2}(t)$ is negligible.

However, if the frequency band of fundamental frequency components of the overlaps with that of second harmonic frequency component 2fo of the transmission signal, the cross-correlation value is higher in proportion to the overlap of the frequency bandwidths, resulting in reduced image quality.

More particularly, the mainlobe width of the compressed weighted chirp signal is inversely proportional to the bandwidth of the weighted chirp signal so that the bandwidth of the weighted chirp signal should be maximized to obtain high image resolution.

However, if the bandwidth of the transmitted weighted chirp signal is wider than half the bandwidth of transducer array 1, the frequency band of fundamental frequency component fo overlaps that of second harmonic frequency component 2fo. In this case, the signal pulse-compressed by second correlator 35 via the harmonic frequency correlation (2fo-correlation) mode will have increased sidelobes due to the cross-correlation between fundamental frequency component fo and the impulse response function h(t) of the second correlator 35, resulting in deteriorated image quality.

Consequently, in this case, the harmonic frequency correlation pulse inversion (2fo-correlation (PI)) mode, through third input terminal (c), is very useful. Harmonic frequency correlation pulse inversion (2fo-correlation (PI)) effectively removes fundamental frequency component fo and simultaneously compresses second harmonic frequency component 2fo, making a harmonic image of maximum SNR and resolution.

However, although the harmonic frequency correlation pulse inversion (2fo-correlation (PI)) mode, through the third input terminal (c), improves the image quality, the harmonic frequency correlation pulse inversion (2fo-correlation (PI)) mode reduces the frame rate more than the harmonic frequency correlation (2fo-correlation) mode.

Thus, if the frame rate is more important than the resolution, the bandwidth of the transmission weighted chirp signal should be properly adjusted within a bandwidth range capable of maintaining a $C_{o2}(t)$ magnitude below −50 dB, which is the requisite minimum for forming a medical ultrasound image. After properly adjusting the bandwidth of the transmission weighted chirp signal, second correlator 35 performs a harmonic frequency correlation (2fo-correlation) and removes fundamental frequency component fo without filtering or pulse inversion, i.e., without reduction in frame rate.

In other words, for forming a harmonic image using second correlator 35, the ultrasound imaging system can selectively employ a harmonic frequency correlation (2fo-correlation) mode or a harmonic frequency correlation pulse inversion (2fo-correlation (PI)) mode depending on the parameter to be optimized (e.g., frame rate or resolution).

Figure 3:
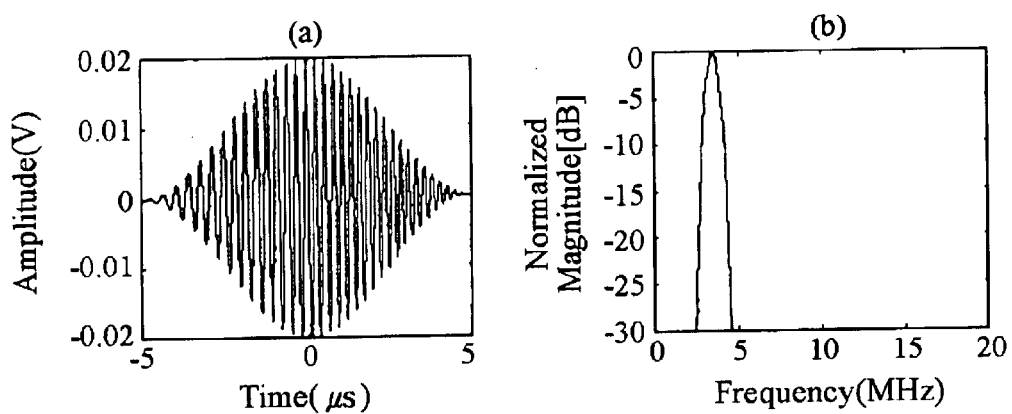
FIG. 3(a) illustrates a transmission weighted chirp signal in accordance with the present invention.
FIG. 3(b) illustrates the spectrum of the transmission weighted chirp signal of FIG. 3(a).

FIG. 3(*a*) illustrates a transmission weighted chirp signal applied to the present invention, and FIG. 3(*b*) illustrates a spectrum of the transmission weighted chirp signal of FIG. 3(*a*).

Figure 4:
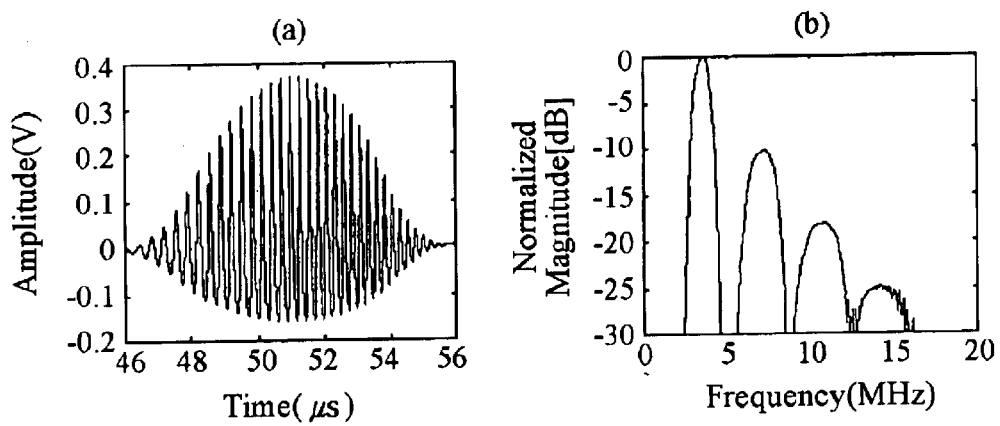
FIG. 4(a) illustrates a received ultrasound signal at a focal length.
FIG. 4(b) illustrates the spectrum of the received ultrasound signal of FIG. 4(a).

FIG. 4(*a*) illustrates the received ultrasound signals at a focal length, and FIG. 4(*b*) illustrates a spectrum of the received ultrasound signals of FIG. 4(*a*).

Referring to FIGS. 3 and 4, the transmitted weighted chirp signal, in accordance with the present invention, has a 30 dB relative bandwidth of 63%. As shown in FIG. 3(*a*), $\Delta\omega/\omega_0 = 0.63$, $2.39 \text{ MHz} \leq \omega \leq 4.61 \text{ MHz}$, and a 10 µs length. Referring to FIG. 3(*b*), fundamental frequency component fo has a center frequency of 3.5 MHz. Referring to FIG. 4(*b*) second harmonic frequency component 2fo appears at 7 MHz. As can be seen from FIGS. 3 and 4, the weighted chirp signal is distorted at one focal length due the harmonics generated by the nonlinear characteristics of the propagating medium.

Figure 5:
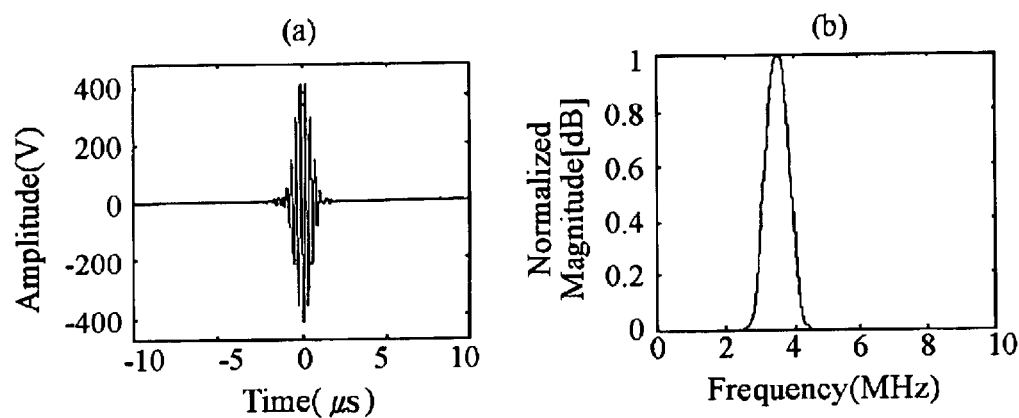
FIG. 5(a) illustrates the received ultrasound signal of FIG. 4(a) as pulse-compressed by a first correlator 34 matched to the fundamental frequency component fo.
FIG. 5(b) illustrates the spectrum of the pulse-compressed signal of FIG. 5(a).

FIG. 5(*a*) illustrates a pulse-compressed signal that the received ultrasound signals of FIG. 4(*a*) is pulse-compressed by a first correlator 34 matched with the fundamental frequency components fo, and FIG. 5(*b*) illustrates a spectrum of the pulse-compressed signal of FIG. 5(*a*).

Figure 6:
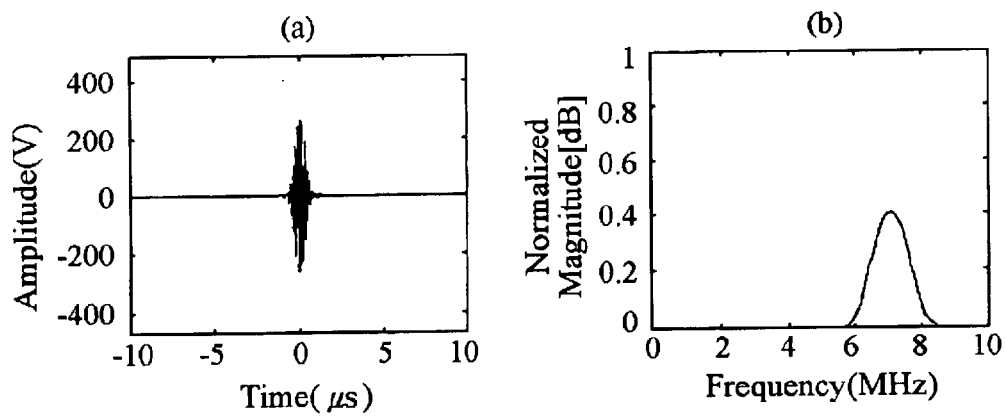
FIG. 6(a) illustrates the received ultrasound signal of FIG. 4(a) as pulse-compressed by a second correlator 35 matched to the harmonic frequency component 2fo.
FIG. 6(b) illustrates the spectrum of the pulse-compressed signal of FIG. 6(a).

FIG. 6(*a*) illustrates a pulse-compressed signal that the received ultrasound signals of FIG. 4(*a*) is pulse-compressed by a second correlator 35 matched with the harmonic frequency components 2fo, and FIG. 6(*b*) illustrates a spectrum of the pulse-compressed signal of FIG. 6(*a*).

Referring to FIGS. 5 and 6, fundamental frequency component fo and second harmonic frequency component 2fo are separated from each other and independently compressed in the fundamental frequency correlation (fo-correlation) mode or the harmonic frequency correlation (2fo-correlation) mode.

Referring to FIG. 5(*a*), the transmission weighted chirp signal of FIG. 3(*a*) is pulse-compressed to ⅕ the original length of the entire signal. Referring to FIG. 6(*a*), the transmission weighted chirp signal of FIG. 3(*a*) is pulse-compressed to ⅛ the length of the original signal.

FIG. 5(*b*) illustrates that a frequency bandwidth of the pulse-compressed signal is identical with that of the transmission weighted chirp signal. FIG. 6(*b*) illustrates that a frequency bandwidth of the pulse-compressed signal is identical with that of a harmonic frequency component of the transmission weighted chirp signal.

Figure 7:
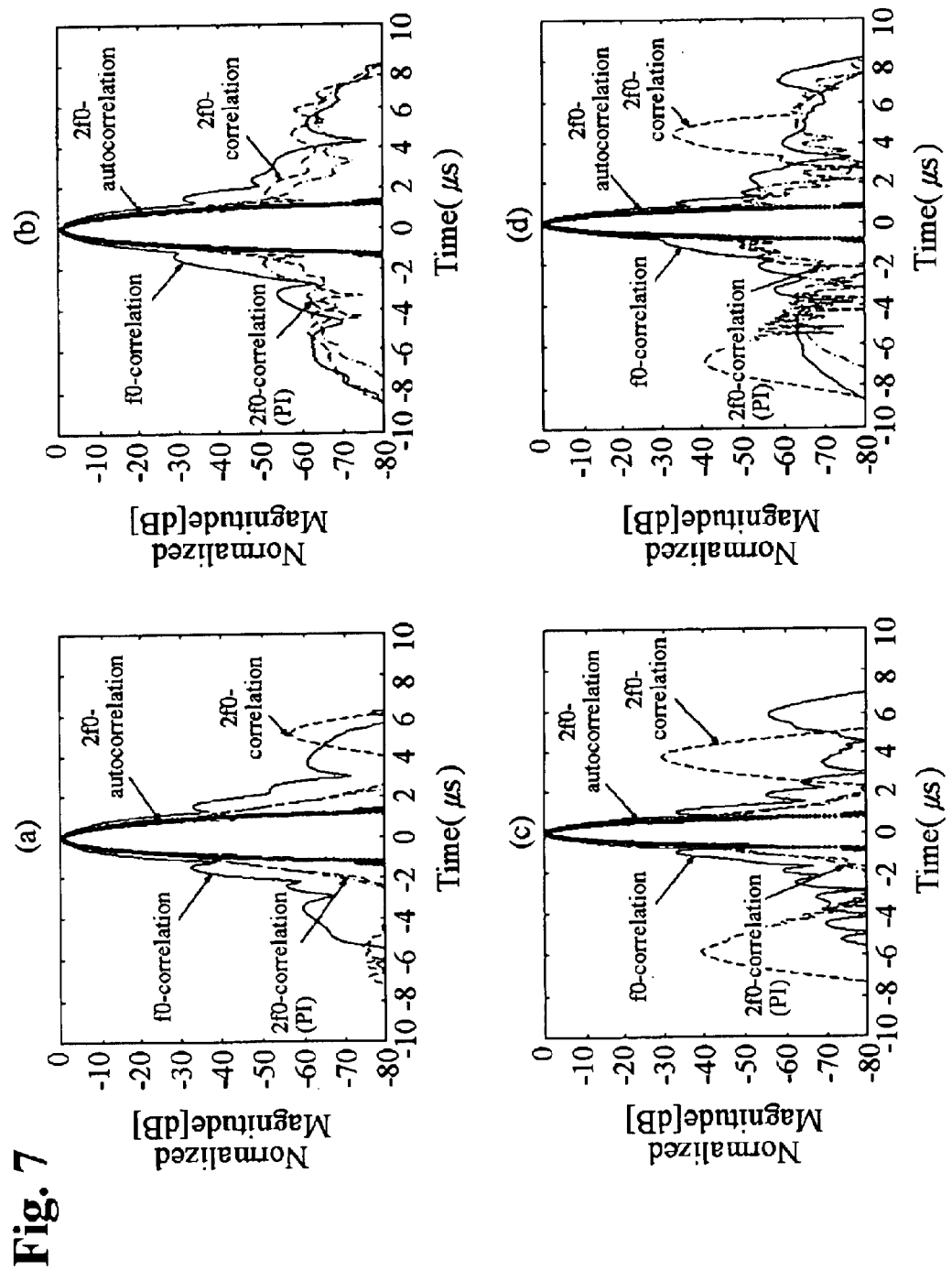
FIG. 7(a) illustrates a pulse compression result that applies a theoretical analysis using the KZK equation with respect to a fundamental frequency correlation (i.e., $f_o$-correlation) step.
FIG. 7(b) illustrates a pulse compression result that applies a theoretical analysis using the KZK equation with respect to a harmonic frequency correlation (i.e., $2f_o$-correlation) step.
FIG. 7(c) illustrates a pulse compression result that applies a theoretical analysis using the KZK equation with respect to a harmonic frequency correlation pulse inversion (i.e., $2f_o$-correlation-(PI)) step.
FIG. 7(d) illustrates a pulse compression result passing through an actual medium.

FIG. 7(*a*) illustrates a pulse compression result that applies a theoretical analysis using KZK equation with respect to a fundamental frequency correlation (i.e., $f_o$-correlation) step, FIG. 7(*b*) illustrates a pulse compression result that applies a theoretical analysis using KZK equation with respect to a harmonic frequency correlation (i.e., $2f_o$-correlation) step, FIG. 7(*c*) illustrates a pulse compression result that applies a theoretical analysis using KZK equation with respect to a harmonic frequency correlation pulse inversion (i.e., $2f_o$-correlation(PI) step, and FIG. 7(*d*) illustrates a pulse compression result passing through an actual medium.

2fo-autocorrelation result of harmonic frequency component 2fo, not including the fundamental frequency component fo, is further inserted in FIGS. 7(*a*)–7(*d*) as a comparing reference among fo-correlation, 2fo-correlation, and 2fo-correlation(PI).

Referring to FIG. 7(*a*), pulse compression simulated with the KZK equation where the 30 dB bandwidth of the transmission weighted chirp signal is at the center frequency of 63% (i.e., $\Delta\omega/\omega_o=0.63$ and $2.39 \text{ MHz} \leq \omega \leq 4.61 \text{ MHz}$). FIG. 7(*b*) illustrates a pulse compression result with respect to the ultrasound signal received at a real focal length under the same conditions as FIG. 7(*a*).

Referring to FIG. 7(*c*), pulse compression simulated with the KZK equation for the case of a transmission weighted chirp signal with a 30 dB bandwidth and center frequency of 89% (i.e., $\Delta\omega/\omega_o=0.89$ and $1.94 \text{ MHz} \leq \omega \leq 5.01 \text{ MHz}$). FIG. 7(*d*) illustrates a pulse compression result with respect to the ultrasound signal received at a real focal length under the same conditions as FIG. 7(*c*).

Referring to FIGS. 7(*a*) and 7(*b*), the bandwidth (2.39 MHz~4.61 MHz) of fundamental frequency component fo barely overlaps with the bandwidth (4.78 MHz~9.22 MHz) of the second harmonic frequency component. Thus, the cross-correlation value, $C_{o2}(t)$, is negligible. As shown in the pulse-compression result of FIG. 7(*a*), the sidelobes of the fo-correlation signal are gradually reduced. Likewise, the sidelobes of the 2fo-correlation signal are gradually reduced to −60 dB.

However, since harmonic frequency component 2fo has a lower energy than fundamental frequency component fo, cross-correlation function $C_{o2}(t)$ has a greater influence on harmonic frequency component 2fo. The sidelobes are increased to −57 dB at a position from the center of the mainlobes by 5 µs. In the case of 2fo-correlation (PI), fundamental frequency component fo has been removed so there is no increase in the sidelobes due to cross-correlation.

The output signal of second correlator 35 through 2fo-correlation and the output signal of second correlator 35 through 2fo-correlation (PI) have a 20 dB mainlobe width of 1.28 µs, which is less than the 1.99 µs mainlobe width of the output signal of first correlator 34. Thus, the bandwidth of harmonic frequency component 2fo is wider than that of fundamental frequency component fo. The mainlobe of the pulse-compressed signal is inversely proportional to the bandwidth of the weighted chirp signal.

Referring to FIGS. 7(*a*) and 7(*b*), although the fundamental frequency components are removed, the mainlobes of the 2fo-correlation (PI) signal and the 2fo-autocorrelation signal diverge in the range of −40 dB and below. For this reason, pulse inversion removes the fundamental frequency component, but not the third and higher harmonic frequency components. However, since the third and higher harmonic frequency components are weak, the 2fo-correlation (PI) signal is similar to 2fo-autocorrelation signal not the 2fo-correlation signal.

Referring to FIG. 7(c), the bandwidth of the fundamental frequency component is 1.94 MHz–5.01 MHz, and the bandwidth of the second harmonic frequency component is 3.88 MHz–10.02 MHz. The bandwidths of the fundamental and harmonic frequency components are larger in FIG. 7(c) than FIG. 7(a). The 20 dB mainlobes of the fo-correlation signal, 2fo-correlation signal, and 2fo-correlation(PI) signal are lower than in FIG. 7(a). The bandwidth overlap between fundamental frequency component fo and harmonic frequency component 2fo increases, thereby increasing the sidelobes of the 2fo-correlation signal to −30 dB. For the 2fo-correlation (PI) signal, fundamental frequency component fo is removed by the pulse inversion so that the sidelobes of the compressed pulse waveform are quickly reduced as in FIG. 7(a).

FIG. 7(b) illustrates a pulse compression of a signal reflected from a real target object corresponding to FIG. 7(a) (i.e., $\Delta\omega/\omega_0=0.63$), and FIG. 7(d) illustrates a pulse compression of a signal reflected from a real target object corresponding to FIG. 7(c) (i.e., $\Delta\omega/\omega_0=0.89$). For the fo-correlation signal, FIG. 7(a) is very similar to FIG. 7(c).

For the 2fo-correlation signal, the 20 dB mainlobe appears at 1.285 μs in FIG. 7(b) and 0.89 μs in FIG. 7(d). These 20 dB mainlobes are very similar to those of FIGS. 7(a) and 7(c). In FIG. 7(b), the maximum sidelobe appears at −57 dB, and in FIG. 7(d), the maximum sidelobe appears at −30 dB. These sidelobes are also similar to FIGS. 7(a) and 7(c).

However, referring to FIGS. 7(a) and 7(c) illustrating simulation results using KZK equation and FIGS. 7(b) and 7(d) illustrating a pulse compression result of the signals reflected from a real target object.

Analysis using the KZK equation approximately models ultrasound propagation in a real target object, and some errors may arise in the pulse compression. In other words, for the purpose of pulse inversion, the two same signals should have a 180° phase difference. However, this condition is actually difficult to satisfy because a some phase difference may arise due to a sampling step or some other circuit irregularity.

Referring to FIGS. 7(b) and 7(d), the sidelobes of the 2fo-correlation (PI) signal are greater than in FIGS. 7(a) and 7(c). However, in all cases, the maximum sidelobes are limited to −60 dB, which is below the level allowable in the medical ultrasound imaging system.

The 2fo-correlation method is useful when the transmitted weighted chirp signals have a bandwidth below a predetermined level. The method can produce the compressed harmonic frequency pulse with only one ultrasound transmission/reception process. Thus, the 2fo-correlation method provides superior frame rate compared to the conventional pulse inversion method.

The 2fo-correlation (PI) method is useful to when using a wideband ultrasound chirp signal for improving frame rate by reducing the mainlobe width of the second harmonic frequency component signal.

Figure 8:
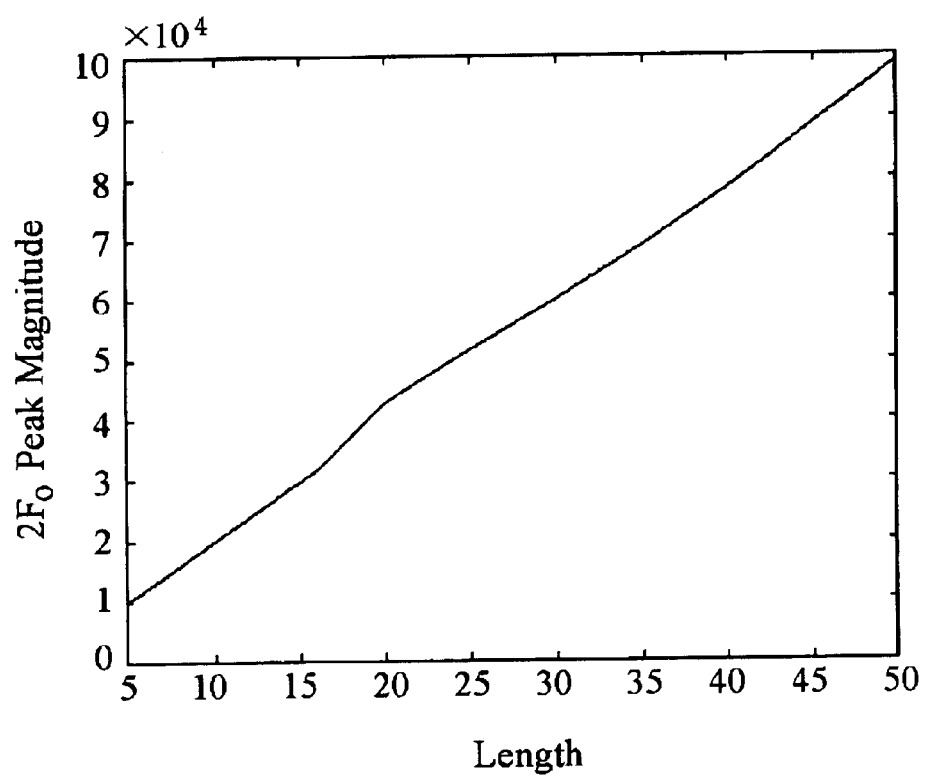
FIG. 8 illustrates the magnitude variation of a second harmonic frequency component with respect to the length of the weighted chirp signal, at a particular sound pressure of the transmission weighted chirp signal of FIG. 3(a).

Referring to FIG. 8, the magnitude of the second harmonic frequency component varies with respect to the length of the weighted chirp signal at a predetermined sound pressure of 210 kPa. The magnitude of harmonic components 2fo increases in proportion to the length of the weighted chirp signal without a saturation limit. Since the magnitude of 2fo increases in proportion to the length of the weighted chirp signal, the SNR of 2fo can be increased by increasing the length of the weighted chirp signal.

The magnitude of harmonic frequency component 2fo increases in proportion to the length of the weighted chirp signal. But the peak voltage of the weighted chirp signal is limited by the electrical characteristics of the transducer array and a potential harm to the human body. In a preferred embodiment, although the peak voltage of the weighted chirp signal is lowered, the length of the weighted chirp signal can be increased by a predetermined length in order to compensate for the lowered peak voltage and thereby increase the magnitude of the harmonic frequency component at a low sound pressure.

$$\left(\frac{TV_1}{TV_2}\right)^2 \times \frac{L_1}{L_2} = 1 \qquad \text{Eq. 8}$$

Eq. 8 illustrates the relationship between two weighted chirp signals having the same 2fo-correlation pulse compression result. In Eq. 8, TV is the transmission voltage, L is the length of the weighted chirp signal, $TV_1$ is the transmission voltage of the first weighted chirp signal, $TV_2$ is the transmission voltage of the second weighted chirp signal, $L_1$ is a length of the first weighted chirp signal, and $L_2$ is the length of the second weighted chirp signal.

Referring to Eq. 8, if the transmission voltage is cut in half, then the length of the weighted chirp signal should be four-times greater. So, if the transmitted weighted chirp signal is four-times in length, then the SNR of the harmonic image corresponding to the original length can be maintained over a 50% voltage drop. Thus, the SNR of the harmonic image can be improved by increasing the length of the weighted chirp signal.

As described, the ultrasound imaging system and method in accordance with the present invention produces a high quality harmonic image by removing fundamental frequency components through pulse-compression using weighted chirp signals and increasing the SNR by extending the length of a transmitted weighted chirp signal without sound pressure saturation.

The ultrasound imaging system and method can form ultrasound images according to a 2fo-correlation method using fundamental frequency components or 2fo-correlation (PI) method using harmonic frequency components. If frame rate is important, then the 2fo-correlation method is employed. If resolution is important, then the 2fo-correlation (PI) method is employed.

While the present invention has been shown and described with respect to the particular embodiments, it will be apparent to those skilled in the art that many exchanges and modifications may be made without departing from the spirit and scope of the invention as defined in the appended claims.

What is claimed is:

1. An ultrasound imaging system comprising:
    a transducer array for converting weighted chirp signals to ultrasound signals, and transmitting the ultrasound signals to a target object;
    a receiver for receiving signals reflected from the target object;
    a pulse-compressor for pulse-compressing harmonic frequency components of the ultrasound signals in the reflected signals;
    means for receive-focusing the pulse-compressed signals; and
    means for producing an ultrasound image on the basis of the receive-focused signal,
    wherein the transducer array further comprises means for increasing a code length of the weighted chirp signal in proportion to a magnitude of the harmonic frequency components at a predetermined sound pressure.

2. The ultrasound imaging system of claim 1 wherein the pulse-compressor further comprises:
    a selector for selecting the harmonic frequency components in the reflected signals; and a correlator for pulse-compressing the selected harmonic frequency components.

3. The ultrasound imaging system of claim 2 wherein the correlator selectively performs a harmonic frequency correlation (2fo-correlation) or a harmonic frequency correlation pulse inversion (2fo-correlation (PI)).

4. The ultrasound imaging system of claim 1 further comprising:

a second pulse-compressor for pulse-compressing fundamental frequency components of the ultrasound signals in the reflected signals.

5. The ultrasound imaging system of claim 4 wherein the second pulse-compressor comprises:

a selector for selecting the fundamental frequency components in the reflected signals; and a correlator for pulse-compressing the selected fundamental frequency components.

6. The ultrasound imaging system of claim 1 wherein the weighted chirp signals are shaped by windowing chirp signals by means of a predetermined window function.

7. An ultrasound imaging method comprising the steps of:

converting weighted chirp signals to ultrasound signals;

transmitting the ultrasound signals to a target object;

receiving signals reflected from the target object;

pulse-compressing harmonic frequency components of the ultrasound signals in the reflected signals;

receive-focusing the pulse-compressed signals; and producing an ultrasound image on the basis of the receive-focused signals, wherein the step of converting further comprises increasing a code length of the weighted chirp signal in proportion to a magnitude of the harmonic frequency components at a predetermined sound pressure.

8. The ultrasound imaging method of claim 7 wherein the pulse-compressing step further comprises:

selecting the harmonic frequency components in the reflected signals; and pulse-compressing the selected harmonic frequency components selected by the selector.

9. The ultrasound imaging method of claim 8 wherein the pulse-compressing step selectively performs a harmonic frequency correlation (2fo-correlation) or a harmonic frequency correlation pulse inversion (2fo-correlation (PI)).

10. The ultrasound imaging method of claim 7 further comprising the step of:

pulse-compressing fundamental frequency components of the ultrasound signals in the reflected signals.

11. The ultrasound imaging method of claim 10 wherein the step of pulse-compressing fundamental frequency components includes the steps of:

selecting the fundamental frequency components in the reflected signals; and pulse-compressing the selected fundamental frequency components.

12. The ultrasound imaging method of claim 7 wherein the weighted chirp signals are shaped by windowing chirp signals by means of a predetermined window function.

13. An ultrasound imaging system comprising:

a transducer array for converting weighted chirp signals to ultrasound signals, and transmitting the ultrasound signals to a target object;

a receiver for receiving signals reflected from the target object;

a pulse-compressor for selectively pulse-compressing fundamental frequency components or harmonic frequency components of the ultrasound signals in the reflected signals;

means for receive-focusing the pulse-compressed signals; and means for producing an ultrasound image on the basis of the receive-focused signals, wherein the transducer array includes means for increasing a code length of the weighted chirp signal in proportion to a magnitude of the harmonic frequency components at a predetermined sound pressure.

14. The ultrasound imaging system of claim wherein the pulse-compressor further comprises:

a first correlator for pulse-compressing the fundamental frequency components;

a second correlator for pulse-compressing the harmonic frequency components; and a mode selector for selecting the fundamental frequency components or the harmonic frequency components in the reflected signals and for enabling the selected frequency components to be pulse-compressed via one of the first and second correlators.

15. The ultrasound imaging system of claim 14 wherein the second correlator selectively performs a harmonic frequency correlation (2fo-correlation) or a harmonic frequency correlation pulse inversion (2fo-correlation (PI)).

16. An ultrasound imaging method comprising the steps of:

converting weighted chirp signals to ultrasound signals, and transmitting the ultrasound signals to a target object;

receiving signals reflected from the target object;

pulse-compressing fundamental frequency components or harmonic frequency components of the ultrasound signals in the reflected signals;

receive-focusing the pulse-compressed signals; and producing an ultrasound image on the basis of the receive-focused signals, wherein the converting step further comprises increasing a code length of the weighted chirp signal in proportion to a magnitude of the harmonic frequency components at a predetermined sound pressure.

17. The ultrasound imaging method of claim 16 wherein the pulse-compressing step further comprises the steps of:

selecting the fundamental frequency components or the harmonic frequency components in the reflected signals; and pulse-compressing the selected frequency components.

18. The ultrasound imaging method of claim 17 wherein the pulse-compressing step includes selectively performing a harmonic frequency correlation (2fo-correlation) or a harmonic frequency correlation pulse inversion (2fo-correlation (PI).

* * * * *